United States Patent [19]

Benson et al.

[11] Patent Number: 5,196,311
[45] Date of Patent: Mar. 23, 1993

[54] ELISA TEST FOR VON WILLEBRAND FACTOR

[75] Inventors: Roger E. Benson, Albany; James L. Catalfamo, South Bethlehem, both of N.Y.; W. Jean Dodds, Santa Monica, Calif.

[73] Assignee: Health Research, Incorporated, Albany, N.Y.

[21] Appl. No.: 428,161

[22] Filed: Oct. 27, 1989

[51] Int. Cl.[5] .................. G01N 33/53; G01N 33/531; G01N 33/543; C07K 15/06

[52] U.S. Cl. ................................ 435/7.94; 435/7.92; 435/7.1; 530/387; 530/389.3

[58] Field of Search ............... 436/518, 7.11; 530/383, 530/387, 389.3; 435/7.94, 7.92, 7.1

[56] References Cited

U.S. PATENT DOCUMENTS

| | | | |
|---|---|---|---|
| 4,376,110 | 3/1983 | David et al. | 436/513 |
| 4,486,530 | 12/1984 | David et al. | 435/7 |
| 4,578,218 | 3/1986 | Saundry et al. | 530/383 |
| 4,666,865 | 5/1987 | Chang et al. | 436/518 |
| 4,687,747 | 8/1987 | Lin | 436/518 |
| 4,748,110 | 5/1988 | Paul | 435/5 |

OTHER PUBLICATIONS

Ardaillou, N., et al., Thrombosis Research 12: 817-830 (1978).
Bartlett, A., et al., Br Med J 1: 994-996 (1976).
Benson, R. E., et al., Thrombosis Research 7: 383-389 (1975).
Benson, R. E., et al., Amer. J. Vet. Research 44: 399-403 (1983).
Benson, R. E., et al., Vet. Immunology & Immunopath. 7: 337-346 (1984).
Benson, R. E. & Dodds, W. J., Vet. Immun. & Immunopath 11:21-30 (1986).
Bowie, E. J. W., et al., Blood 62: 146-151 (1983).
Bradley, L. A., et al., Clin. Chem. 30: 87-92 (1984).
Brien, W. F., & Stewart, M. W., Clin. Biochemistry 19:179-182 (1986).
Brown, J. E., & Bosak, J. O., Thrombosis Research 43:303-311 (1986).
Casonato, A., & Girolami, A., Folia Haematol. 113: 670-684 (1986).
Cejka, J., Clin. Chem. 28: 1356-1358 (1982).
Fishman, D. J., et al., Blood 59: 1163-1168 (1982).
Furlong, R. A., et al., Clin. lab. Haemat. 10: 295-305 (1988).
Handin, R. I. & Wagner, D. D., Progress in Hemostasis and Thrombosis 9: 233-259 (1989).
Ingerslev, J., Scand J Clin Lab Invest 47: 143-149 (1987).
Ingerslev, J., et al., Clinica Chimica Acta 174: 65-82 (1986).
Inoue, K., et al., Chem. Pharm. Bull. 34: 2550-2554 (1986).
Katzmann, J. A., et al., Blood 58: 530-536 (1981).

Mascelli, M. A., et al., Biochemistry 25: 6325-6335 (1986).
Mascelli, M. A., & Kirby, E. P., Biochemistry 27: 1274-1284 (1988).
Meyers, K. M., et al., Thrombosis Research 57: 109-116 (1990).
Ness, P. M., & Perkins, H. A., Thrombos.Haemostas. 42:848-853 (1979).
Ogata, K., et al., Blood 61: 27-35 (1983).
Peake, I. R., & Bloom, A. L., Thrombosis Research 10: 27-32 (1977).
Rodeghiero, F., et al., Blood 69: 454-459 (1987).
Short, P. E., et al., Medical Lab. Sciences 39: 351-355 (1982).
Silveira, A. M. V., et al., Thrombosis Research 43: 91-102 (1986).
Taylor, L. D., Thrombosis and Haemostasis 59: 251-254 (1988).
Wang, H. X., et al., J Clin Pathol 38: 317-319 (1985).
Yamamoto, T., et al., Thrombosis Research 45: 59-74 (1987).
Yorde, L. D., et al., Clin. Chem. 25: 1924-1927 (1979).
Zimmerman, T. S., et al., J. Lab. Clin. Med. 86: 152-159 (1975).
Zimmerman, T. S., et al., J. Clin. Investigation 50: 244-254 (1971).
Bennett, B. and Ratnoff, W. D., Proc Soc Exp Biol Med 143: 701-706 (1973).
Benson, R. E., & Dodds, W. J., Br J Haematol 31: 437-446 (1975).
Bouma, B. N., et al., Scand J Haematol 17: 263-275 (1976).
Clowes, A. W., et al., Lab Invest 39: 141-149 (1978).
Coppola, R., et al., Thrombosis Research 17: 473-480 (1980).
Cotter, S. M., et al., J. Am Vet Med Assoc 172: 166-168 (1978).
Griggs, T. R., et al., Proc Nat Acad Sci USA 74: 759-763 (1977).
Johnson, G. S., et al., Thrombosis Research 42: 419-423 (1986).
Meyer, D., et al., Br J Haematol 57: 597-608 (1984).
Nachman, R., et al., J Clin Invest 60: 914-920 (1977).
Olson, J. D., et al., J Lab Clin Med 89: 1278-1293 (1977).
Schmer, G., et al., J Biol Chem 247: 2512-2521 (1972).

(List continued on next page.)

Primary Examiner—Christine M. Nucker
Assistant Examiner—M. P. Woodward
Attorney, Agent, or Firm—Heslin & Rothenberg

[57] ABSTRACT

Novel polyclonal antibodies useful for measuring von Willebrand Factor in plasma of various vertebrate species either qualitatively or quantitatively, methods of producing and using such antibodies and kits containing them are described.

17 Claims, No Drawings

OTHER PUBLICATIONS

Turitto, V. T., et al., Blood 65: 823–831 (1985).
Verweij, C. et al., EMBO J. 5:1839–1847 (1986).
Pietu, G. et al., Biochem Biophys Res Comm 163:618–626 (1989).
Bahou, W. et al., J Clin Invest 84:56–61 (1989).
Brinkhous, K. et al., EMBASE Abstract No. 86008826 of Semin Throm Hemost 11:337–341 (1985).
Chand, S. et al., EMBASE Abstract No. 86198216 of Throm Haemostasis 55:318–324 (1986).
Thorsen, L. et al., EMBASE Abstract No. 84035971 of Throm Haemostasis 57:212–216 (1987).
Silverman, C. et al., J Lab Clin Med 110:113–118 (1987).
Benjamin, D. C. et al., HYBRIDOMA 6:183–190 (1987).

ELISA TEST FOR VON WILLEBRAND FACTOR

FIELD OF THE INVENTION

This invention is concerned with measurement of the von Willebrand Factor (vWF), a multimeric glycoprotein which plays an essential role in the hemostatic process.

BACKGROUND OF THE INVENTION

Factor VIII/vWF is a plasma coagulation complex composed of two differently sized, noncovalently linked, and genetically independent proteins. The higher molecular weight component that is involved in platelet-vessel wall interactions is termed vWF. It is deficient and/or defecrive in the inherited bleeding disorder, von Willebrand,s disease (vWD). The lower molecular weight component, factor VIII-coagulant (VIII:C), is deficient and/or defective in the inherited disorder, hemophilia A. Many acquired disease states can also exhibit low levels of vWF and VIII:C. In contrast, elevated levels of vWF and VIII:C are associated with acute and chronic inflammatory diseases, cancers and thrombotic states.

The process of this invention utilizes antibodies having novel properties in new qualitative and quantitative tests to permit immunologic measurement of vWF. The process is particularly useful in screening assays which may be performed in a general laboratory or clinical setting without the need of expensive equipment or a highly trained staff.

The method will be employed to determine whether humans and other vertebrates are at risk to bleed during surgery or other stress situations caused by inherited or acquired vWD, or for gene*ically transmitting vWD. It can also be used to measure vWF levels in individuals experiencing or at risk to develop thrombotic states, cancers, and acute and chronic inflammatory disorders.

No simple immunological screening assay for vWF or vWD has heretofore been available, although sophisticated quantitative assays of vWF are performed in large biomedical and commercial laboratories.

vWD is one of the most common inherited bleeding disorders of man and domestic animals Recent estimates of gene frequently of inherited vWD in humans range from 1 in 5000 to as high as 1 in 50 live births of either sex. Within purebred dog families, prevalence can be as high as 70% (Doberman pinschers) and varies between 15% and 45% in many breeds.

vWF is a very large glycoprotein which plays an important role in reactions of platelets with the vessel wall. It is usually deficient in vWD. The laboratory diagnosis of vWD is dependent on demonstrating decreased levels of plasma vWF. When measured immunologically, this property of vWF is termed vWF antigen (vWF:Ag) and will be so identified hereinafter.

Quantitative determination of plasma vWF:Ag by electroimmunoassay (EIA) or radioimmunoassay (RIA) is currently an important tool to determine whether an individual is affected with congenital, inherited or acquired vWD. The Veterinary Hematology Laboratory of the State of New York Department of Health routinely analyzes vWF:Ag levels by EIA of more than 7,500 samples per year of humans, dogs and other species.

The novel process of this invention utilizes a double antibody Enzyme-Linked Immunosorbent Assay (ELISA) to determine vWF:Ag. The process is easy to perform, efficient, accurate and highly sensitive. It is applicable to humans, nonhuman primates, dogs, horses, pigs, mice, rats, guinea pigs, rabbits, cows, and cats and other vertebrates. These animals are valuable as pets, food sources, work animals, zoological exhibits, and for research. No procedure has heretofore been described in which the same antibodies have been successfully employed with such a large number of species.

Physicians and veterinary clinicians have become increasingly aware of the prevalence of vWD as a cause or precipitating factor in abnormal bleeding and consequently the demand for a practical screening test for vWD has arisen. The process of this invention provides such a test.

Silveira et al (Thrombosis Research 43; 91-102, 1986) have described a sandwich ELISA system to measure plasma vWF:Ag in humans. The test utilizes antibodies to human vWF:Ag raised in rabbits. The rabbit antibody is immobilized in the wells of a microtiter plate and acts as the reactive capture surface for vWF:Ag. Serially diluted plasma samples containing either known or unknown levels of vWF:Ag are reacted with the immobilized antibody, and then quantified by detection with a second (sandwich) antibody to human vWF:Ag (goat antihuman vWF:Ag) and a horseradish peroxidase-conjugated porcine antigoat IgG. The peroxidase activity generated by the final antibody is proportional to the captured amount of vWF:Ag and is measured by the color change it catalyses in the substrate orthophenylenediamine (OPD). The color change reaction is subsequently quenched with sulfuric acid and the optical density measured to determine the concentration of vWF:Ag in the plasma tested.

A disadvantage of the above process is that the rabbit and goat antibodies to vWF which function as the initial capture, immobilizing or anchor antibody and the second or sandwich antibody are raised against human vWF:Ag. Because the original source material for preparing human vWF:Ag is human blood, it presents the danger of transmitting blood-borne diseases to other humans. As a result, the test should only be employed in specially equipped and sanitized laboratories designated for handling specimens of human origin (CDC—Guidelines for prevention of transmission of human immunodeficiency virus and hepatitis B virus to healthcare and public-safety workers. MMWR. 38, (S-6); Jun. 23, 1989, pp. 1-37).

The process of the present invention does not depend upon the utilization of vWF:Ag from humans to raise antibodies. Moreover, and most unexpectedly, the antibodies utilized in the invention are highly species cross-reactive and can be employed to test for vWF:Ag in a wide range of vertebrates, especially mammals.

THE INVENTION

Novel antibodies have now been discovered which can be used in the ELISA procedure to test for the presence and concentration of vWF:Ag in a wide variety of species. These antibodies are raised against canine vWF:Ag and purified by adsorption with the plasma proteins of canines homozygous for vWD. The purified antibodies can be employed qualitatively or semiquantitatively in screening tests for vWF:Ag or for sensitive and specific quantitative determination of this protein in vertebrates such as mammals, including humans. The antibodies may be provided in a variety of kits which may additionally contain associated reactants, normal and abnormal comparison plasmas and standards.

It is essential for the performance of this ELISA to employ antibodies which will adhere or stick to an insoluble substrate surface, e.g. the surface of the microtiter plate wells or other container in which the test is carried out. The antibodies of this invention are sticky proteins which will adhere firmly to the substrate surface. So far as is known, no antibodies to canine vWF:Ag have heretofore been known which are sufficiently sticky for use in a highly sensitive and accurate ELISA procedure.

DETAILED DESCRIPTION OF THE INVENTION

The presently preferred method for carrying out the process of this invention is:

1: Utilizing purified canine vWF:Ag, raise antibodies to canine vWF:Ag (hereinafter, anticanine vWF:Ag) in selected vertebrate species such as rabbits or goats.

2: Coat the surface of the reaction vessel, suitably the well of a microtiter plate with the anticanine vWF:Ag to serve as the capture, immobilizing or anchor antibody.

3: Add the test plasma containing an unknown quantity of vWF:Ag to the test vessel.

4: Add a second anticanine vWF:Ag to the reaction vessel. This is the sandwich antibody and should be different from the capture antibody, i.e. raised in a different species. For example, if the capture antibody is raised in a rabbit, the sandwich antibody may be raised in a goat, or vice versa.

5: Add a detectant for the sandwich antibody, for example, an enzyme-conjugated anti IgG to the reaction vessel. This reagent should be reactive with the sandwich antibody used in step 4 (i.e. raised against the same species), but not reactive with the capture antibody. For example, it should be antigoat IgG if the sandwich antibody was raised in a goat.

6: Detect the amount of vWF:Ag in the unknown plasma by measuring the amount of antibody-conjugated detectant. For example, if the detectant is an enzyme which produces a color reaction, the intensity of the color, i.e. the optical density of the color produced can be utilized to determine the amount of vWF:Ag in the unknown either qualitatively or quantitatively.

Those skilled in the art will recognize the foregoing outline as a description of a modified ELISA procedure. They will recognize also that the generalized outline omits certain of the specific steps such as serial dilution and washing with appropriate buffers which are standard in the ELISA procedure. Although specific buffers and other reagents will be described hereinafter, and specific dilutions will be employed to llustrate the invention, the skilled artisan will recognize that these are illustrative only and that many equivalents are possible.

The operation of this invention, especially in the qualitative (i.e. screening) mode requires the selection of a standard vWF:Ag concentration to which one or more concentrations of known standards and the plasma, the concentration of which is to be determined will be compared The standard may be prepared as described below. A convenient single standard is 65% (0.65 unit/ml) of the plasma vWF:Ag level of healthy individuals (hereinafter called normal plasma and assigned a value of 100% or 1 u/ml), which may be selected for purposes of comparison with other plasmas. The assay can be made semiquantitative by selecting several reference standards having vWF:Ag levels such as 15% (0.15 u/ml), 35% (0.35 u/ml), and 65% (0.65 u/ml) of normal. These levels are selected for the presently preferred practice of the invention because extensive experience with EIA testing of healthy individuals of several species has indicated that the lower limit for the normal range is about 60% (0.6 u/ml). A person or animal is statistically at low risk for bleeding during surgery or other stress situations and is unlikely to transmit vWD to progeny if the level of vWF:Ag is at least 60% (0.6 u/ml). Individuals with levels of less than 60% (0.6 u/ml) require special caution. The methods of this invent ion are useful in genetic surveillance in a breeding program to reduce or eliminate the prevalence of vWD in various animal species such as dogs, cats, horses, nonhuman primates, and other domestic, laboratory or exotic animals.

An essential aspect of this invention is the availability of a species born with zero level of vWF:Ag, i.e. a species whose plasma contains no, or essentially no vWF:Ag. Such mammals (e.g. humans, dogs, pigs) are available and can be identified, for example, by standard EIA tests for vWF:Ag and then confirmed by a more sensitive test like that of the present invention, another ELISA, RIA, or immunoelectro-blotting. Plasma from such people or animals will contain all of the antigens other than vWF found in the plasma of healthy normal members of the species, and therefore can be used to remove contaminants thereby purifying the anti vWF:Ag of this invention by standard adsorption procedures such as those illustrated below.

There follows a complete description of the various steps utilized in the practice of this invention. The specific procedures are given by way of illustration only and should not be considered as limitations of the invention.

ISOLATION AND PURIFICATION OF CANINE vWF:Ag

The vWF:Ag was purified by cryoconcentration and molecular exclusion chromatography. The procedures are generally well known in the art. Canine blood was collected in 3.8% trisodium citrate (10% V/V) and the plasma was made cell-free by centrifugation at 2,000 and 12,000 xg. The plasma was stored in 100 ml aliquots at −40° C. until used.

Four 100 ml aliquots were thawed slowly overnight at 4° C. The following morning the plasma with the suspended cryoprecipitate was dispensed in 40 ml aliquots in Nalgene test tubes and 53% ethanol was added and mixed to a final concentration of 3%. The tubes were placed in a methanol-water ice bath at −3° C. for 30 minutes and then centrifuged at 12,000 x g for 10 min at 4° C. The supernatant plasma was discarded and the precipitate taken up in 3 ml of phosphate buffered saline (PBS), pH 7.4.

This concentrate was further purified by loading on a 2.5×40 cm 2% agarose column and elution at 20 ml/hr at room temperature with PBS into 5 ml fractions which were stored at 4° C. The fractions were analyzed for vWF:Ag by EIA overnight and the four peak fractions, typically containing 10–12 u/ml vWF:Ag were pooled and filtered over a 2.5×40 cm 6% agarose column, eluted as above. The five peak fractions, usually containing in excess of 5 u/ml of purified vWF:Ag were pooled, dispensed in 0.5 ml aliquots and stored at '140° C.

IMMUNIZATION OF VERTEBRATES (RABBITS OR GOATS) WITH CANINE vWF:Ag: PREPARATION OF HETEROLOGOUS ANTICANINE vWF:Ag

Antisera to canine vWF:Ag were raised in Chinchilla-Flemish Giant NYS:(FG) rabbits and a pooled Alpine grade goat. Aliquots of the purified antigen prepared as described above were thawed and mixed with an equal volume of 2% Al(OH) diluted 1:10 with sterile saline. The fur on each 3-6 month old rabbit's back was clipped and the area thoroughly cleaned before each inoculation. A loading dose of 2 ml of the vWF:Ag-Al(OH)$_3$ mixture was injected intradermally in several sites, followed by serial booster doses of 1 ml at weekly intervals for 4 weeks. Five weeks after the loading dose, 50 ml of rabbit blood were collected by ear artery puncture and then serum harvested as described below.

Antiserum was also raised in a single 4-year-old goat. Four ml of the purified vWF:Ag was mixed with an equal volume of Al(OH)$_3$ as above and injected intradermally into the clipped back of the goat. The goat was immunized at half the loading dose seven additional times over a period of two months and 400 ml of blood were collected by jugular puncture.

The goat and rabbit blood were separately collected in 16×125 mm glass tubes and clotted at 37° C. for one hour and overnight at 4° C. The contracted red cell clots were detached and the serum decanted and centrifuged to remove residual cells. The goat and rabbit antisera thus prepared were each incubated at 56° C. to inactivate complement and residual coagulation factors were adsorbed with Ca$_3$(PO$_4$)$_2$ (10 mg/ml) to provide antisera ready for the next adsorption step to prepare the antibodies of the invention.

ADSORPTION OF ANTISERA: PURIFICATION OF ANTICANINE vWF:Ag

Citrated canine plasma from dogs homozygous for vWD was used to prepare a cryoprecipitate free of vWF:Ag for use as an adsorbent for equal volumes of the antisera prepared in the previous step. The antiserum (rabbit or goat) was added to the cryoprecipitate and incubated for one hour at 37° C. and overnight at 4° C. The adsorbed antiserum was centrifuged at 10,000 g for about 10 minutes at 4° C. the following day to remove precipitated material. Each antiserum was adsorbed a second time with an equal volume of adsorbent to prepared a serum from which contaminant precipitable antibodies were removed and other contaminant antibodies neutralized.

Each serum thus prepared contains antibody of the invention and is employed in the following purification step.

PREPARATION OF ANTICANINE vWF:Ag

The preparations of the previous step were precipitated three times with half saturation of aqueous (NH$_4$)$_2$SO$_4$ to produce PBS globulins. The globulins were extensively dialyzed versus PBS and then 0.01M Tris buffer (pH 8.0) to remove residual (NH$_4$)$_2$SO$_4$. Approximately 100 mg. of globulrn fraction, after dialysis, was applied to a 2.5×40 cm DEAE Sepharose column and eluted with a gradient of 0.1 M Tris-HCl, pH 8.0, and ending with the same buffer containing 0.3M sodium chloride (pH 8.0). The peak fractions containing the heterologous rabbit or goat anticanine vWF:Ag IgG were identified in the EIA (Laurell rocket assay) or the ELISA assay respectively using normal canine and homozygous canine vWD plasmas.

The peak fractions thus prepared contain the purified antibodies of the invention. The fractions can be used directly in the process of the invention.

EVALUATION OF SPECIFICITY OF IgG FOR CANINE vWF

The rabbit IgG containing antibodies to canine vWF:Ag was evaluated for specificity by being cast in agarose gels and generating precipitin rockets in the EIA against normal canine plasma, but failing to generate detectable precipitin reactions against plasma from dogs homozygous for vWD. The immune goat IgG to canine vWF:Ag did not form precipitin rockets against normal canine plasma in the EIA, thereby demonstrating the differing physicochemical properties of these two novel antibodies to the same protein. However, when microtiter plates were coated initially with the rabbit anticanine vWF:Ag IgG and the goat anticanine vWF:Ag IgG was used as the second (sandwich) antibody, normal dog plasma strongly reacted whereas plasma from dogs homozygous for vWD failed to react and behaved like the buffer blanks. Antisera which were not absorbed with homozygous vWD plasma prior to evaluation by this ELISA assay generated optical density readings higher than the buffer blanks (i.e. contained non VWF contaminants).

The antibodies of the invention from different species, therefore, differ to some extent in physicochemical properties. However, they react similarly in the ELISA assay with canine plasma to detect vWF:Ag.

PREPARATION OF BUFFERS AND OTHER REAGENTS

Coating Buffer - (10x stock solution) - Dilute 1:10 before use
21.2 g Na$_2$CO$_3$  0.01 g Thimerosal (Bacteriostat) check pH equals 9.6 - adjust with NaOH or HCl
33.6 g NaHCO$_3$  dilute up to 1.0 liter
Buffer Added After Coating
4.5 NaCl in 450 ml distilled water
0.5 mg Thimerosal
1000 mg bovine serum albumin (BSA)
adjust to pH 7.4 using 1 mole/l Tris base
dilute up 0.5 liter (500 ml)
PBS-Tween Buffer - (10x stock solution) - Dilute 1:10 before use
80.1 g NaCl  50 ml Tween 20
2.0 g KCl  10 mg Thimerosal
9.46 g Na$_2$HPO$_4$  check pH - adjust to 7.4 with NaOH or HCl
2.0 g KH$_2$PO$_4$  dilute up to 1.0 liter
ELISA Dilution Buffer (10x-Stock) Dilute 1:10 and pH to 7.4 with
1 molar Tris-base (approximately 3.0 ml)
90. g NaCl
5.0 g BSA
10 mg Thimerosal
10.6 g disodium EDTA (FW 372.24)
dilute to 1 liter
Citrate Buffer - (10x stock solution) - Dilute 1:10 before use
63.6 citric acid  check pH equals 5.0 - adjust with NaOH or HCl
97.1 g Na$_2$HPO$_4$  dilute up to 1.0 liter
0.01 g Thimerosal
Ortho-Phenylenediamine (OPD) - Substrate Solution - Make fresh just before use.
30 mg OPD tablet (Sigma Chemical Co., St. Louis, Mo.)
33 ml citrate buffer
150 μl of 3% H$_2$O$_2$
Sulfuric Acid (H$_2$SO$_4$) 4.5 mole/l -continued 125 ml concentrated H₂SO₄ added slowly to 375 ml of water Tris Base 1 mole/l 121.1 g Tris-base diluted up to 1.0 liter

QUALITATIVE AND SEMIQUANTITATIVE ELISA SCREENING PROCEDURES

Strip Preparation: Test strips (e.g. Duo-Strips containing eight wells available from Dynatech Corporation, Alexandria, VA) are coated with 100 μl/well of capture (e.g. rabbit) antibody to canine vWF:Ag appropriately diluted (e.g. 1:500) with coating buffer. Coating is usually completed for many strips at once. The strips are stacked and incubated overnight in a humid, 37° C. incubator. The top strips are covered by tape. The following day, the plates are washed 3 times with PBS-Tween buffer, 200 ul in each well.

Buffer Added After Coating: 150 μl of after coating (saline-albumin) buffer is added to each well and incubated 1 hour at room temperature or at 4° C. and stored for up to two months, when the strips are tape-sealed. Immediately prior to the addition of plasma dilutions, the strips are washed three fold with pBS-Tween as above.

Plasma Dilutions: The single standard pooled plasma (which has been prepared to contain 65% (0.65 u/ml) vWF:Ag, or several standards prepared to contain 15% (0.15 u/ml), 35% (0.35 u/ml) as well as 65% (0.65 u/ml) vWF:Ag, are diluted 1:100 in dilution buffer. The normal and abnormal control plasmas and unknown samples are also diluted 1:100. The normal plasma serves as a control to monitor the system. The abnormal control is 0% vWF:Ag.

Addition of plasma to Strip Wells of a Microtiter Plate

A. Standard Plasmas: 100 μl of the 15% (0.15 u/ml), 35% (0.35 u/ml) and/or 65% (0.65 u/ml) standard plasma dilutions are added to the first, third, and fifth wells either in series or in replicate strips.

B. Unknown Plasma: 100 μl of the diluted unknown plasma is added to the second, fourth, and sixth wells.

C. Normal and Abnormal Control Plasmas: 100 μl of the normal control is added to the seventh well and 100μl of the abnormal control is added to the eighth well.

When the plasma dilutions are complete, the plate is sealed with tape and incubated for one hour at room temperature in the dark.

Strip Washing: The plasma dilutions are washed from the wells three times with 200 μl of PBS-Tween.

Addition of Second (Sandwich) Anticanine vWF:Ag: Following the washing with PBS-Tween, 100 μl of second (e.g. goat) anticanine vWF:Ag appropriately diluted (e.g. 1:1000) in dilution buffer is added to each well and the sealing tape is replaced. The strip is incubated for one hour at room temperature in the dark.

Strip Washing: The strips are washed three times with PBS-Tween as above.

Addition of Detector Anti-Immunoqlobulin (Anti Sandwich IgG): 100 ul/well of peroxidase-conjugated antibody (e.g. porcine antigoat IgG) appropriately diluted (e.g. 1:4000) in dilution buffer is added. The sealing tape is replaced and the strip is incubated at room temperature for one hour in the dark.

Plate Washing: The plate is washed three times with PBS-Tween as above.

Citrate Buffer Spray: Using an aerosol can the strip is sprayed with citrate buffer three times and is shaken to drain its washings into a sink.

Color Reaction with OPD: Following the spray step, 100 μl of the OPD-H₂O₂ solution is added to each well. After approximately 10 minutes the reaction is terminated by adding 100 μl/well of 4.5 M H₂SO₄.

Unknown Comparisons and Controls: Under standard indoor fluorescent lighting, place the well strips over a white background (3×5 inch card works well) and compare the color intensity of the three wells containing the 65% (0.65 u/ml) vWF:Ag standard or the series of 15% (0.15 u/ml), 35% (0.35 u/ml), and 65% (0.65 u/ml) standards to the unknown samples which are in alternate wells in triplicate. The objective of the comparison is to determine if the unknowns are of more, less, or of equal color intensity than the standards. The normal control plasma is assigned 100% (1 u/ml) vWF:Ag and should be obviously of greater color intensity that the 15%, 35% or 65% standards while the abnormal control plasma known to be genetically homozygous deficient in vWF has less than 0.002% ($0.2 \times 10^{-4}$ u/ml) vWF:Ag and should have no color.

The strip may be read with an ELISA reader at 490 nm with the abnormal control plasma serving as the blank. Comparison of the quantitative optical desities of the triplicate or serial standards and the triplicate unknown sample virtually eliminates any uncertainty of visual comparisons and permits definitive quantitation of the unknown vWF:Ag level.

Interpretation: The color intensity of the unknown is graded as being stronger than, equal to or of lesser color intensity than the standards. Experience with a very large number of such qualitative tests has made it clear that visual comparison readily defines three or more groups of unknown plasma vWF:Ag levels; e.g. below 20% (0.2 u/ml), 30-40% 0.3-0.4 u/ml), 60-75% (0.60-75 u/ml), and greater than 80% (0.8 u/ml).

Using these screening determinations, the clinician or animal breeder can quickly determine if a sample has plasma levels less than or greater than 70-75% (0.7-0.75 u/ml) vWF:Ag. Patients with vWF:Ag levels above 75% are at little or no risk for surgical or other bleeding caused by reduced levels of vWf:Ag or are unlikely to transmit vWD to their offspring.

Those samples which are determined to be approximately equal to or less than 75% vWF:Ag should be followed up by referral for a quantitative confirmatory vWF:Ag assay in a research, biomedical or commercial laboratory. Plasma from individuals that generate virtually no color reaction are affected with vWD.

QUANTITATIVE ELISA PROCEDURE

This procedure utilizes the EL 312 ELISA Plate Reader available from Bio-Tek Instruments, Winooski, VT. However, the procedure is not limited to this specific instrument, as will be evident to those skilled in the art.

Plate Preparation

Microtiter plates with 96 wells (e.g. 96 plate Immulon I, Dynatech Corporation) are coated with 100 μl/well of rabbit anticanine vWF:Ag (the DEAE purified fractions prepared as described above) appropriately diluted (e.g. 1:500) with coating buffer. Fifteen plates are usually coated at once. The plates are stacked and incubated overnight in a humid, 37° C. incubator. The top plate is covered by an empty plate. The following day, the plates are washed 3 times with PBS-Tween buffer.

Buffer Added After Coating

200 μl of freshly prepared after-coating buffer is added to each well and incubated 1 hour at room temperature, or at 4° C. for up to two months when the plates are tape-sealed.

Dilution Standards

A pooled plasma from healthy individuals of the species being tested is diluted to create a series of standards [100% (u/ml), 50% (0.5 u/ml), 25% (0.25 u/ml), 12.5% (0.125 u/ml), and 6.25% (0.0625 u/ml)] to which the unknown sample plasmas will be compared. Six or more tubes are prepared and designated as standards (labelled $STD_1$, $STD_2$, $STD_3$, $STD_4$, and $STD_5$ and a blank is prepared. To the $STD_1$ add 10.0 ml of dilution buffer, to the other standards add 1.0 ml (1000 ul) of dilution buffer. 50 microliters (μl) of the 100% standard is added to 10.0 ml of the dilution buffer in $STD_1$ tube and the tube is capped with Parafilm (3M Corporation) and inverted gently six times—this is a 1:200 dilution. Next, 1000 ul of the 1:200 dilution is added to 1000 μl of dilution buffer in the $STD_2$ tube which equals a 1:400 dilution. With the pipetting device mix the $STD_2$ six times and then add 1000 μl of the mixed $STD_2$ to the $STD_3$, tube and mix as above. Add 1000 μl of the $STD_3$ tube to the $STD_4$ tube and mix; add 1000 μl of $STD_4$ to the $STD_5$ tube and mix. Add 1 ml of dilution buffer to the blank tube.

Dilution of Unknown Samples

One dilution tube for each unknown sample is prepared with buffer before the plasma is pipetted. The tube labeled 1:600 has 12 ml of buffer. The dilution tubes are lined up behind the plasma samples in the test tube rack.

Using a fresh pipette tip for eacn unknown plasma sample, 20 μl of the plasma sample is added to the 12 ml (1:600 dilution) and capped with fresh Parafilm and inverted six times.

Each unknown plasma sample is similarly diluted. An internal control (reference) plasma of known vWF:Ag level can also be used and diluted similarly. Samples with low and/or no detectable vWF:Ag should also be included on the plate as abnormal controls to assure the specificity, validity, and accuracy of the test.

Addition of Plasma to Wells

Immediately prior to the addition of plasma dilutions to the plates, the wells are washed three times with PBS-Tween, 200 μl/well. 100 μl of each sample is added per well. Dilutions are run in triplicate for each standard. The unknowns are run in triplicate and are distributed on the plate as in the Master Chart shown below. The additions are planned in advance and the Chart is used as a guide. When the plasma additions are complete, the plate is sealed with tape or otherwise covered and stored at 4° C. overnight.

The Master Chart shown below gives the results of an actual test with canine plasma. In the Master Chart, boxes 1-24 are samples to be tested. The boxes marked '83' contain the internal reference plasma having a known value of 83% (0.83 u/ml) vWF:Ag. 'Blk' is the buffer blank. The boxes marked "Std" are the standard plasma dilutions. The boxes marked "Sple" are the unknown sample plasmas. "AC" is the abnormal control (homozygous vWF:Ag deficient plasma).

Plate Washing

The plasma dilutions are drained from the wells which are then washed three times with PBS-Tween after the overnight step and between each antibody incubation.

Addition of Second (Sandwich) Anticanine vWF:Ag

Following the washing with PBS-Tween, add to each well 100 ul of second (e.g. goat) anticanine vWF:Ag appropriately diluted (e.g. 1:1000) in dilution buffer and replace the sealing tape or cover. Incubate for one hour at room temperature in the dark.

Plate Washing

Three washings with PBS-Tween as above.

Addition of Detector Anti-Immunoqlobulin (Anti Sandwich IgG)

Add 100 μl /well of peroxidase-conjugated antibody (e.g. porcine antigoat IgG) appropriately diluted (e.g. 1:4000) in dilution buffer. Replace the sealing tape or cover and incubate at room temperature for one hour in the dark.

Plate Washing

Three washings with PBS-Tween as above.

Citrate Buffer Spray

Using an aerosol can, spray the plate (6–10 inches away) with citrate buffer three times and vigorously shake the plate's washings into a sink after each spray.

Color Reaction with OPD

Following the spray step, 100 μl of the $OPD-H_2O_2$ substrate is added to each well with a multichannel pipetting device and fresh tips. After approximately 10 minutes, the reaction is terminated by adding 100 μl/well of the 4.5 M $H_2SO_4$. The pipette tips do not need to be changed between the OPD and $H_2SO_4$.

Plate Scanning

The top of the plate is wiped dry with a lint-free pad and inserted in an ELISA plate reader and a report form with final results in generated. These results are summarized on the following Master Chart.

An examination of the chart is convincing of the accuracy of the test as shown by the low deviations in the readings listed in different boxes for the same compositions. Compare, for example $STD_1$ in boxes A-1, A-12 and H-12, or 83 REF in boxes A-6 and H-6.

The optical densities are converted to percent vWF:Ag by comparison with the quadratic curve generated from the triplicate values of the five standards using a soft ware package from the instrument manufacturer.

The following Master Chart consolidates all of the above information including sample numbers, machine readings and percent of vWF:Ag per standard, reference or sample.

| | 1 | 2 | 3 | 4 | 5 | 6 | 7 | 8 | 9 | 10 | 11 | 12 |
|---|---|---|---|---|---|---|---|---|---|---|---|---|
| | | | | | | MASTER CHART | | | | | | |
| A | STD 1 | STD 2 | STD 3 | STD 5 | STD 5 | 83 Ref | 83 Ref | BLK | BLK | STD 3 | STD 2 | STD 1 |
| | 1.182 | 0.997 | 0.773 | 0.597 | 0.446 | 0.729 | 0.774 | 0.225 | 0.223 | 0.735 | 0.951 | 1.269 |
| | | | | | | 71% | 80% | | | | | |
| B | Sple 1 | Sple 1 | Sple 1 | Sple 2 | Sple 2 | Sple 2 | Sple 3 | Sple 3 | Sple 3 | Sple 4 | Sple 4 | Sple 4 |
| | 0.869 | 0.862 | 0.785 | 0.767 | 0.758 | 0.765 | 0.549 | 0.572 | 0.561 | 0.614 | 0.642 | 0.663 |
| | 103% | 101% | 83% | 79% | 77% | 79% | 37% | 41% | 39% | 49% | 54% | 58% |
| C | Sple 5 | Sple 5 | Sple 5 | Sple 6 | Sple 6 | Sple 6 | Sple 7 | Sple 7 | Sple 7 | Sple 8 | Sple 8 | Sple 8 |
| | 0.296 | 0.280 | 0.261 | 0.646 | 0.658 | 0.623 | 0.537 | 0.517 | 0.528 | 0.733 | 0.737 | 0.788 |

-continued

MASTER CHART

| | 1 | 2 | 3 | 4 | 5 | 6 | 7 | 8 | 9 | 10 | 11 | 12 |
|---|---|---|---|---|---|---|---|---|---|---|---|---|
| | 0% | 0% | 0% | 55% | 57% | 50% | 35% | 31% | 33% | 72% | 73% | 84% |
| D | Sple 9 | Sple 9 | Sple 9 | Sple 10 | Sple 10 | Sple 10 | Sple 11 | Sple 11 | Sple 11 | Sple 12 | Sple 12 | Sple 12 |
| | 0.845 | 0.745 | 0.706 | 0.248 | 0.269 | 0.264 | 0.705 | 0.687 | 0.706 | 0.635 | 0.648 | 0.731 |
| | 97% | 74% | 66% | 0% | 0% | 0% | 66% | 63% | 66% | 53% | 55% | 71% |
| E | Sple 13 | Sple 13 | Sple 13 | Sple 14 | Sple 14 | Sple 14 | Sple 15 | Sple 15 | Sple 15 | Sple 16 | Sple 16 | Sple 16 |
| | 0.690 | 0.659 | 0.657 | 0.358 | 0.356 | 0.361 | 0.732 | 0.688 | 0.716 | 0.281 | 0.303 | 0.319 |
| | 63% | 57% | 57% | 6% | 5% | 6% | 72% | 63% | 68% | 0% | 0% | 0% |
| F | Sple 17 | Sple 17 | Sple 17 | Sple 18 | Sple 18 | Sple 18 | Sple 19 | Sple 19 | Sple 19 | Sple 20 | Sple 20 | Sple 20 |
| | 0.924 | 0.922 | 0.853 | 0.318 | 0.327 | 0.320 | 0.378 | 0.355 | 0.361 | 0.369 | 0.375 | 0.490 |
| | 117% | 116% | 99% | 0% | 1% | 0% | 9% | 5% | 6% | 7% | 8% | 27% |
| G | Sple 21 | Sple 21 | Sple 21 | Sple 22 | Sple 22 | Sple 22 | Sple 23 | Sple 23 | Sple 23 | Sple 24 | Sple 24 | Sple 24 |
| | 0.972 | 0.927 | 0.902 | 0.843 | 0.836 | 0.840 | 0.616 | 0.584 | 0.549 | 0.627 | 0.614 | 0.666 |
| | 118% | 118% | 111% | 96% | 95% | 96% | 49% | 43% | 37% | 51% | 49% | 58% |
| H | STD 4 | STD 5 | AC | AC | AC | 83 Ref | BLK | STD 5 | STD 4 | STD 3 | STD 2 | STD 1 |
| | 0.688 | 0.499 | 0.231 | 0.214 | 0.241 | 0.768 | 0.251 | 0.484 | 0.624 | 0.783 | 1.001 | 1.071 |
| | | | 0% | 0% | 0% | 79% | | | | | | |

The specificity, accuracy and reproducibility of the process of this invention will be readily apparent from inspection of the Master Chart.

The wide applicability of the test will be apparent from standard curves prepared as described above in which optical density is plotted against the reciprocals of the dilutions different species. These curves could be employed in accordance with the invention to determine the concentration of vWF:Ag in unknown samples from each of the species.

The polyclonal antibodies of this invention, although differing in certain physicochemical properties have a number of properties in common which contribute to their utility for the practice of the invention. One of the most important of these properties is that in the coating buffer they are sticky and will adhere firmly to a surface useful in the ELISA test. Another is that they form soluble reaction complexes with vWF:Ag from a wide variety of species. Still another is that individually they react with labeled detectant antibodies (anti IgG). For example, goat anti vWF:Ag will react specifically with porcine antigoat IgG but not with porcine antirabbit IgG. Thus in the ELISA test of the invention the detector-IgG reacts with the sandwich antibody not with the capture antibody to form a soluble detectable product comprising the capture antibody, the vWF:Ag, the sandwich antibody and the labeled detectant IgG. It is the solubility of the various reactant products formed during the test which makes the invention operable.

The process of the invention whether applied qualitatively or quantitatively, comprises the steps of:

1. adhering a first capture antibody, which is an anticanine vWF:Ag of the invention to an insoluble immunological reaction surface, 2. contacting, under immunological reaction conditions, the adhered, capture antibody with the sample to be tested for the presence and concentration of vWF:Ag to form, if vWF:Ag is present in the sample, an immobilized and soluble antibody/antigen complex, 3. contacting, under immunological reaction conditions, the thus formed immobilized antibody/antigen product with a second sandwich antibody which is an anticanine vWF:Ag of the invention to form an immobilized and soluble antibody/antigen/antibody complex, the sandwich antibody having been raised in a vertebrate species different from the capture antibody, 4. contacting, under immunological reaction conditions, the antibody/antigen/antibody complex with a reactive detector immunoglobulin raised against immunoglobulin from the same species as the sandwich antibody, and 5. detecting the reaction product.

Immunological reaction surfaces and immunological reaction conditions are terms well known and understood to those skilled in the art.

An immunological reaction surface is a surface which is insoluble in the reacting medium and on which immunological reactions take place, for example reactions involved in the ELISA procedure. Typically they are glass or plastic such as polystyrene or polyacrylate. The surface may be the interior surface of a test tube, the well of a microtiter plate or some other container suitable for an immunological reaction. Those skilled in the art will know of other appropriate surfaces on which an immunological reaction can take place, e.g. glass or plastic beads or rods. For the purposes of this reaction, the surface will be one to which the antibodies of the invention will adhere.

Immunological reaction conditions are conditions with respect to temperature, concentration, solvent, pH, etc. under which an immunological reaction such as the formation of an antibody/antigen complex will take place. Those skilled in the art are thoroughly familiar with the parameters under which such complexes will form. They will know that the temperature cannot be so high or the pH so extreme as to inactivate the reactant. The solvent is typically a selected buffer or other carrier for the reactants. It may be plasma, serum or some fraction of these materials. The reaction products, including the intermediate reaction products of this invention are soluble in the reaction solvent.

The antibodies of this invention are sticky polyclonal antibodies raised against canine vWF:Ag, bur reactive with vWF:Ag from other vertebrate species, purified by adsorption with the plasma proteins from dogs homozygous for vWS. The antibodies are useful in methods for determining the presence and quantity of vWF:Ag in vertebrate plasma by contacting the antibody with the plasma to be tested in a reaction mixture under immunological reaction conditions and thereafter determining if an immunological reaction, i.e. a reaction between the antibody (antivWF:Ag) and antigen (vWF:Ag) in the plasma has taken place by an appropriate procedure.

The extent of the immunological reaction can be determined qualitatively or semiquantitatively by Visual comparison of the optical density of unknown samples with known standards or quantitatively by spectrophotometric comparison with standard curves prepared using a number of samples of known vWF:Ag concentration.

Although the procedure of the invention has been specifically described for purposes of illustration utilizing a detector anti-immunoglobulin (antisandwich IgG) conjugated with horseradish peroxidase and orthophenylenediamine dihydrochloride color reagent, other detector reagents can also be employed. These include, for example, tetramethyl benzidine as a peroxidase substrate.

Antisandwich IgG conjugated to alkaline phosphatase can also be used. An effective and convenient substrate is paranitrophenyl phosphate (PNPP) which, like OPD, is available commercially in tablet form. The enzyme reaction of alkaline phosphatase and PNPP can be stopped with concentrated NaOH, and the yellow color is quite stable and can be assessed visually or photometrically at 405 nm. Other compounds of this class having the appropriate molar absorptivity and solubility characteristics are also appropriate substrates.

Immunoglobulin linked to N-hydroxysuccinimidobiotin (i.e., biotin) can also be effective probes for sandwich anti vWF:Ag when reacted with a detector (avidin-horseradish peroxidase). The peroxidase substrates identified above would be used to generate the color endpoint.

The color detectros are most convenient for utilizing the antivWF:Ag of the invention, but the invention is not so limited. Other detection systems including isotopic or electrochemical labels can also be employed.

The various reactants and reagents employed in the practice of this invention may be conveniently provided in kits suitable for use by the physician or veterinarian, or for use in clinical and research laboratories. Such kits will contain a capture antibody of the invention together with a sandwich antibody and a detector IgG together with at least one plasma of known vWF:Ag concentration, e.g. the 65% standard plasma or 83% reference plasma described above together with an abnormal control plasma, i.e. a substantially 0% vWF:Ag plasma. If the test is intended for quantitative use, it will additionally contain a sufficient number of standard plasmas to construct a reference curve. For example, it could contain a 15%, 30% and 45% plasma. Either of the kits may also contain an internal normal control plasma of known concentration which can be used to confirm the integrity of the system. The kit will also contain a detector IgG which will react with the sandwich antibody under immunological reaction conditions.

One very convenient form of kit for use of the invention comprises a microtiter plate with an antibody of the invention adhered to the surface of each well.

Additional reagents utilized in the practice of the invention may be provided in the kit, but most conveniently will be maintained as stock reagents in the laboratory. These include dilution buffer, washing buffer, citrate buffer, OPD or similar detectors, dilute sulfuric acid and hydrogen perioxide.

What is claimed is:

1. A polyclonal antibody against canine von Willebrand factor antigen that is useful for measuring von Willebrand factor antigen in vertebrate plasma, wherein said vertebrate plasma is isolated from a vertebrate species selected from the group consisting of at least three of human, nonhuman primate, dog, horse, pig, mouse, rat, guinea pig, rabbit, cow and cat and wherein said polyclonal antibody is isolted by (1) isolating and purifying von Willebrand factor antigen from canines, (2) immunizing a vertebrate species with the isolated and purified canine von Willebrand factor antigen, so as to produce polyclonal antibody against canine von Willebrand factor antigen in the vertebrate species, (3) isolating the polyclonal antibody against canine von Willebrand factor antigen from the vertebrate species, and (4) purifying the isolated polyclonal antibody against canine von Willebrand factor antigen by adsorption with plasma isolated from canines homozygous for von Willebrands disease.

2. An antibody of claim 1 raised in a rabbit.

3. An antibody of claim 1 raised in a goat.

4. A process for determining the presence of von Willebrand factor antigen in a sample vertebrate plasma comprising the steps of:

a) contacting a capture antibody which is an antibody of claim 1 with a sample vertebrate plasma to be tested for the presence of von Willebrand factor antigen to form, if von Willebrand factor antigen is present in the sample vertebrate plasma, a first complex, said first complex comprising the capture antibody and the von Willebrand factor antigen, wherein the vertebrate plasma is from a vertebrate species selected from the group consisting of human, nonhuman primate, dog, horse, pig, mouse, rat, guinea pig, rabbit, cow, and cat;

b) contacting the thus formed first complex with a sandwich antibody which is an antibody of claim 1 to form a second complex, said second complex comprising the capture antibody, the von Willebrand factor antigen, and the sandwich antibody, the sandwich antibody having been raised in a vertebrate species different from the vertebrate species in which the capture antibody had been raised;

c) contacting the second complex with a reaction detector immunoglobulin raised against immunoglobulin from the same species in which the sandwich antibody was raised, so as to form a third complex, and d) detecting the third complex.

5. The process of claim 4 wherein the capture antibody is an antibody raised in a rabbit.

6. The process of claim 4 wherein the sandwich antibody is an antibody raised in a goat.

7. The process of claim 4 wherein the capture antibody is an antibody raised in a goat.

8. The process of claim 4 wherein the sandwich antibody is an antibody raised in a rabbit.

9. The process of of claim 4 wherein the capture antibody is an antibody raised in a rabbit and the sandwich antibody is an antibody raised in a goat.

10. The process of claim 4 wherein the capture antibody is an antibody raised in a goat and the sandwich antibody is an antibody raised in a rabbit.

11. A kit for sue in measuring von Willebrand factor antigen in vertebrate plasma, the vertebrate plasma being from a vertebrate species selected from the gruop consisting of human, nonhuman primate, dog, horse, pig, mouse, rat, guinea pig, rabbit, cow, and cat, said kit comprising a polyclonal capture antibody against canine von Willebrand factor antigen, wherein said polyclonal antibody is isolated by (1) isolating and purifying von Willebrand factor antigen from canines, (2) immunizing a vertebrate species with the isolated and purified canine von Willebrand factor antigen, so as to produce polyclonal antibody against canine von Willebrand factor antigen in the vertebrate specieis, (3) isolating the polyclonal antibody against canine von Willebrand factor antigen from the vertebrates pecies, and (4) purifying the isolated polyclonal antibody against canine von Willebrand factor antigen by adsorption with plasma isolated from canines homozygous for von Willebrands disease; the kit also comprising a polyclonal sandwich antibody against canine von Willebrand factor antigen raised in a second vertebrate specieis different from the first vertebrate species and similarly isolated and purified; at least one standard plasma of known von Willebrand factor antigen concentration; an abnormal control plasma substantially free of von Willebrand factor antigen; and a reaction detector immunoglobulin.

12. A kit as in claim 11 wherein the capture antibody is an antibody raised in a rabbit.

13. A kit as in claim 11 wherein the sandwich antibody is an antibody raised in a goat.

14. A kit as in claim 11 wherein the capture antibody is an antibody raised in a goat.

15. A kit as in claim 11 wherein the sandwich antibody is an antibody raised in a rabbit.

16. A kit as in claim 11 wherein the capture antibody is an antibody raised in a rabbit and the sandwich antibody is an antibody raised in a goat.

17. A kit as in claim 11 wherein the capture antibody is an antibody raised in a goat and the sandwich antibody is an antibody raised in a rabbit.

* * * * *

UNITED STATES PATENT AND TRADEMARK OFFICE
CERTIFICATE OF CORRECTION

PATENT NO. : 5,196,311
DATED : March 23, 1993
INVENTOR(S) : Roger E. Benson et al.

It is certified that error appears in the above-identified patent and that said Letters Patent is hereby corrected as shown below:

In column 1, line 2, before "FIELD OF THE INVENTION" add the following:
--This invention was made with support under the National Institute of Health, National Heart Lung Blood Institute Grant No. HL 09902. Accordingly, the U.S. Government has certain rights in this invention.--

In claim 1, column 14, line 1, change "isolted" to --isolated--.

In claim 11, column 14, line 58, change "sue" to --use--.

In claim 11, column 14, line 60, change "gruop" to --group--.

In claim 11, column 15, line 2, change "specieis" to --species--.

In claim 11, column 15, line 4, change "vertebrates pecies" to --vertebrate species--.

In claim 11, column 15, line 10, change "specieis" to --species--.

Signed and Sealed this

Eighth Day of March, 1994

*Attest:*

BRUCE LEHMAN

*Attesting Officer*  Commissioner of Patents and Trademarks